US006123931A

United States Patent [19]
Ellingson et al.

[11] Patent Number: 6,123,931
[45] Date of Patent: *Sep. 26, 2000

[54] POLYURETHANE AND POLYACRYL NAIL POLISH COMPOSITIONS

[75] Inventors: Peter Christopher Ellingson, Hamilton; Edward Dewey Smith, III, Mason, both of Ohio

[73] Assignee: The Procter & Gamble Company, Cincinnati, Ohio

[ * ] Notice: This patent is subject to a terminal disclaimer.

[21] Appl. No.: 09/071,424

[22] Filed: May 1, 1998

[51] Int. Cl.⁷ .............................. A61K 7/04; A61K 6/00; A61K 7/00; A61K 47/30; A61K 47/32
[52] U.S. Cl. .......................... 424/61; 424/401; 514/772; 514/773
[58] Field of Search ..................... 424/61, 401; 514/772, 514/772.3

[56] References Cited

U.S. PATENT DOCUMENTS

| | | | |
|---|---|---|---|
| 4,277,380 | 7/1981 | Williams et al. | 260/18 |
| 4,431,763 | 2/1984 | Reed | 524/389 |
| 4,442,259 | 4/1984 | Isgur et al. | 524/839 |
| 4,766,005 | 8/1988 | Montgomery et al. | 427/4 |
| 4,812,492 | 3/1989 | Eckes et al. | 523/351 |
| 5,120,529 | 6/1992 | Koch et al. | 424/61 |
| 5,206,011 | 4/1993 | Pappas et al. | 424/61 |
| 5,538,717 | 7/1996 | La Poterie | 424/61 |
| 5,607,665 | 3/1997 | Calello et al. | 424/61 |
| 5,681,550 | 10/1997 | Rubino | 424/61 |
| 5,716,603 | 2/1998 | Chen et al. | 424/61 |
| 5,811,084 | 9/1998 | Busch, Jr. et al. | 424/61 |

FOREIGN PATENT DOCUMENTS

| | | |
|---|---|---|
| 87242557 | 8/1987 | Canada . |
| 0 061348 A1 | of 0000 | European Pat. Off. . |
| 0 022452 A1 | 1/1981 | European Pat. Off. . |
| 0 325038 A2 | 7/1989 | European Pat. Off. . |
| 0 418469 A1 | 3/1991 | European Pat. Off. . |
| 0 627212 | 5/1993 | European Pat. Off. . |
| 0 619111 A1 | 12/1994 | European Pat. Off. . |
| 0299758 B1 | 12/1994 | European Pat. Off. . |
| 0 636361 | 2/1995 | European Pat. Off. . |
| 0 637600 A1 | 2/1995 | European Pat. Off. . |
| 0 658609 A1 | 6/1995 | European Pat. Off. . |
| 0 679384 | 11/1995 | European Pat. Off. . |
| 0 680742 A1 | 11/1995 | European Pat. Off. . |
| 0 705594 A1 | 4/1996 | European Pat. Off. . |
| 0 797977 A1 | 10/1997 | European Pat. Off. . |
| 57-23632 | 2/1982 | Japan . |
| 4-103512 | 4/1992 | Japan . |
| 4-103513 | 4/1992 | Japan . |
| 4-103514 | 4/1992 | Japan . |
| 5-148122 | 6/1993 | Japan . |
| 5-155737 | 6/1993 | Japan . |
| 5-310531 | 11/1993 | Japan . |
| 7-309721 | 11/1995 | Japan . |
| 9 -157135 | 6/1997 | Japan . |
| 9-268113 | 10/1997 | Japan . |
| 883078 | 11/1981 | U.S.S.R. . |
| WO 96/34061 | 10/1996 | WIPO . |
| WO 97/00664 | 1/1997 | WIPO . |
| WO 97/42930 | 11/1997 | WIPO . |

OTHER PUBLICATIONS

U.S. application No. 09/070,960, Ellingson et al., filed May 1, 1998.
U.S. application No. 09/071,098, Ellingson et al., filed May 1, 1998.
U.S. application No. 09/071,097, Smith et al., filed May 1, 1998.
U.S. application No. 09/071,273, Ellingson et al., filed May 1, 1998.
U.S. application No. 09/071,423, Ellingson et al., filed May 1, 1998.
U.S. application No. 09/,071,099, Ellingson et al., filed May 1, 1998.

*Primary Examiner*—John Kight
*Assistant Examiner*—D. Faulkner
*Attorney, Agent, or Firm*—Darryl C. Little; Loretta J. Henderson

[57] ABSTRACT

The present invention relates to compositions useful as cosmetic or therapeutic agents, as well as methods of their use. The compositions herein are particularly useful as coatings for mammalian nails. More particularly, the present invention relates to compositions which, when applied to mammalian nails exhibit long wear properties including excellent adhesion to the nail.

17 Claims, No Drawings

POLYURETHANE AND POLYACRYL NAIL POLISH COMPOSITIONS

TECHNICAL FIELD

The present invention relates to compositions useful as cosmetic or therapeutic agents and films formed from the compositions. The compositions herein are particularly useful as polishes for mammalian nails, and are especially useful as basecoat compositions.

BACKGROUND OF THE INVENTION

Consumers use nail polishes to cosmetically enhance their nails or protect the nails from everyday conditions and stressors. However, these nail polish compositions are deficient in many respects, including their inability to provide long wear. Nail polishes which are known or currently available often exhibit deterioration, particularly in the form of chipping or peeling, in as few as one or two days. Such poor wear often forces consumers to remove their nail polish soon after original application and reapply additional nail polish to the nails. Consumers may also attempt to correct the unsightly appearance of the deteriorating nail polish by "touching-up" the areas of the nail which exhibit the deterioration, a practice which actually impairs the overall look of the nail polish. Finally, consumers may choose to do nothing about the deterioration and allow, for example, chipping and peeling to progress, resulting in nails which are not only minimally protected from the environment but are unsightly as well.

The art is replete with nail polish compositions which are promoted as having long wear, good adhesion, and/or resistance to chipping. While some nail polish compositions provide better wear than others, a need remains for nail polish compositions providing excellent long wear. It would therefore be desirable to provide nail polish compositions having improved wear properties including, for example, improved adhesion to the nail.

Extreme examples of nail polish compositions which exhibit inadequate wear and adhesion are those which are easily and completely peeled or stripped off the nails without the use of a solvent. See. e.g., EP 0,680,742, Mellul et al., assigned to L'Oreal.

Still further, other poorly adhesive nail polish compositions are completely removable with water and, therefore, are not practical for normal use and do not provide long wear properties under everyday conditions. See, e.g., JP 05-155, 737, Itsumi et al., assigned to Yuho Chemical Co. Ltd. and EP 0,679,384, Ramin et al., assigned to L'Oreal.

The present inventors have surprisingly discovered compositions which form films exhibiting long wear at a superior level not provided by the nail polishes which are presently known and used. Such compositions are particularly useful as basecoat compositions which, when applied to mammalian nails, provide highly adhesive basecoats.

SUMMARY OF THE INVENTION

The present invention relates to compositions which, when applied to mammalian nails, form films exhibiting long wear. Such compositions are especially useful as basecoat compositions. The present compositions comprise:
(a) from about 0.1% to about 40%, by weight of the composition, of a water- insoluble film-forming polymer selected from the group consisting of polyacryls, polymethacryls, polyurethane-polyacryl mixtures, polyurethane-polymethacryl mixtures, urethane-acryl copolymers, and mixtures thereof;
(b) from about 10% to about 90%, by weight of the composition, of a volatile organic solvent; and
(c) water;
wherein when the film-forming polymer is a polyurethane-polyacryl mixture, the composition comprises less than about 1% of iso-propanol and wherein when the composition comprises from about 10% to about 30%, by weight of the composition, of the organic solvent, the composition is substantially free of a fluorinated polymer.

DETAILED DESCRIPTION OF THE INVENTION

The essential components of the present invention are herein described below. Also included are non-limiting descriptions of various optional and preferred components useful in the compositions of the present invention.

The present invention can comprise, consist of, or consist essentially of any of the required or optional components and/or limitations described herein.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for materials including, but not limited to, polymers and optional components. The inventors herein do not intend to be limited by materials under a certain trade name. Equivalent materials (e.g. those obtained from a different source under a different name or catalog (reference) number) to those referenced by trade name may be substituted and utilized in the kits, films, and methods herein.

All documents referred to herein, including all patents, patent applications, and printed publications, are hereby incorporated by reference in their entirety.

The compositions of the present invention are suitable for use as a nail polish for mammalian nails. As used herein, the term "suitable for use as a nail polish for mammalian nails" means that the compositions, or films thereof, are suitable for use in contact with mammalian nails without undue toxicity, incompatibility, instability, allergic response, and the like.

As used herein, the term "nail polish" is a comprehensive term describing a nail polish composition, film, product (including coloring products), system, kit, or the like, which is useful for providing, for example, aesthetic, therapeutic, or prophylactic benefits to the nail.

As used herein, the term "mammalian nail" means a keratinaceous plate present at the upper surface of the end of a finger or toe of a primate, most preferably a human, or the homologous claw or hoof of another mammal.

The layers and films herein may be joined to mammalian nails. As used herein, the terms "joined to", "joined to mammalian nails", or the like means in contact with or applied to a mammalian nail through physical forces in such a manner that the layer or film is contiguous to either the nail itself, a preceding layer, a succeeding layer, or matter previously applied to or existing on the nail. The layer or film may be "joined to" a mammalian nail, preceding layer, or succeeding layer even though other matter (such as another preceding or succeeding layer) intervenes. Accordingly, matter which is "joined to", for example, a mammalian nail, need not actually be contiguous to that mam nail.

As used herein, the term "contiguous to" means directly joined to by physical forces through touching and boundary sharing with essentially no intervening matter.

As used herein, the term "film" means one or more layers of a nail polish suitable for use on mammalian nails which forms when one or more compositions is applied to, and dries on, mammalian nails.

As used herein, the term "layer" means one substantially dry coat of nail polish which forms when a composition is applied to, and dries on, a mammalian nail.

As used herein, the term "preceding layer" means a layer which is joined to a nail and is closer in proximity to the nail as compared to a reference layer joined to the same nail. For example, wherein a basecoat and a topcoat are joined to a nail, the basecoat is a preceding layer relative to the topcoat. Similarly, wherein a basecoat, midcoat, and topcoat are joined to a nail, the basecoat and midcoat are preceding layers relative to the topcoat, and the basecoat is a preceding layer relative to both the midcoat and topcoat.

As used herein, the term "succeeding layer" means a layer which is joined to a nail and is further in proximity from the nail as compared to a reference layer joined to the same nail. For example, wherein a basecoat and a topcoat are joined to a nail, the topcoat is a succeeding layer relative to the basecoat. Similarly, wherein a basecoat, midcoat, and topcoat are joined to a nail, the midcoat and topcoat are succeeding layers relative to the basecoat, and the topcoat is a succeeding layer relative to both the basecoat and midcoat.

As used herein, the term "substantially dry" in reference to a film or a layer means that the film or layer feels dry, smooth, or not tacky when it is touched with a human fingertip.

Compositions of the Present Invention

The present inventors have discovered compositions which, when applied to mammalian nails, form films exhibiting long wear. The present compositions are particularly useful as basecoat compositions which form basecoats when applied to mammalian nails. Additional nail polishes, including midcoat compositions and/or topcoat compositions may be applied to the present basecoats to provide aesthetic (e.g., color) and/or additional performance (e.g., wear) benefits.

As used herein, a "basecoat composition" is a composition which is suitable for application to a mammalian nail to form a basecoat, which is a layer of nail polish. A basecoat composition is preferably applied contiguously to a mammalian nail with or without, more preferably with, one or more succeeding layers applied to the resulting basecoat. The basecoat composition is preferably applied contiguously to a mammalian nail with one or more, more preferably one (topcoat), and most preferably two (midcoat and topcoat), succeeding layers joined to the resulting basecoat.

Without intending to be limited by theory, it is believed that the compositions of the present invention are beneficial to long wear because they afford basecoats providing a preferred level of adhesion to the nail. Such adhesion is believed to be due to physical forces, rather than chemical bonding to the nail. As is known in the art, these physical forces include non-covalent interactions such as polar, non-polar, hydrogen bonding, and charged interactions as well as physical interactions such as mechanical interlocking.

Each of the present compositions comprises a water-insoluble (at ambient temperature and pressure) film-forming polymer, a carrier suitable for application to mammalian nails comprising a liquid diluent, and, optionally, one or more other suitable components as described herein. As used herein, the term "film-forming polymer" means a homopolymer, copolymer, or mixture thereof which forms an adherent continuum from a composition when applied to mammalian nails. See e.g. *Polymer Colloids,* Robert M. Fitch, ed., N.Y.: Plenum Press, pp. 173–183 (1971). As used herein, the term "copolymer" includes linear, block, branched, graft, comb, and star copolymers.

The compositions comprise from about 0.1% to about 20%, more preferably from about 1% to about 15%, still more preferably from about 1% to about 10%, and most preferably from about 2% to about 6% of the film-forming polymer (polymer solids), by weight of the composition. The compositions of the present invention further comprise a liquid diluent. The liquid diluent comprises from about 10% to about 90% of one or more volatile organic solvents, by weight of the composition. The balance of the compositions is substantially water, preferably at least about 4%, more preferably from about 4% to about 85%, still more preferably from about 10% to about 80%, and most preferably from about 25% to about 80%, by weight of the composition, of water.

The film-forming polymers herein are preferably, but are not limited to, solvent-borne or water-borne polymers. As used herein, the term "water-borne", with reference to a film-forming polymer, means that the polymer was prepared in a mixture comprising water and is preferably added to the composition which it comprises as a mixture (preferably a dispersion) in water. As used herein, the term "solvent-borne", with reference to a film-forming polymer, means that the polymer was prepared under substantially anhydrous conditions and is preferably added to the composition which it comprises as a substantially anhydrous mixture (preferably a solution).

Preferred film-forming polymers are selected from polyacryls, polymethacryls, polyurethane-polyacryl mixtures, polyurethane-polymethacryl mixtures, urethane-acryl copolymers, and mixtures thereof. As used herein, a "polyacryl" means a polyacrylate, polyacrylic, or polyacrylamide. As used herein, a "polymethacryl" means a polymethacrylate, polymethacrylic, or polymethacrylamide.

Preferred polyurethanes are selected from aromatic polyether polyurethanes, aliphatic polyether polyurethanes, aromatic polyester polyurethanes, aliphatic polyester polyurethanes, aromatic polycaprolactam polyurethanes, and aliphatic polycaprolactam polyurethanes. The more preferred polyurethanes are selected from aromatic polyether polyurethanes, aliphatic polyether polyurethanes, aromatic polyester polyurethanes, and aliphatic polyester polyurethanes. Examples of preferred polyurethanes include Sancure 2710® and/or Avalure UR 445® (which are equivalent copolymers of polypropylene glycol, isophorone diisocyanate, and 2,2-dimethylolpropionic acid, having the International Nomenclature Cosmetic Ingredient name "PPG-17/PPG-34/IPDI/DMPA Copolymer"), Sancure 878®, Sancure 815®, Sancure 1301®, Sancure 2715®, Sancure 1828®, Sancure 2026®, Sancure 1818®, Sancure 853®, Sancure 830®, Sancure 825®, Sancure 776®, Sancure 850®, Sancure 12140®, Sancure 12619®, Sancure 835®, Sancure 843®, Sancure 898®, Sancure 899®, Sancure 1511®, Sancure 1514®, Sancure 1517®, Sancure 1591®, Sancure 2255®, Sancure 2260®, Sancure 2310®, Sancure 2725®, and Sancure 12471® (all of which are commercially available from BFGoodrich, Cleveland, Ohio), Bayhydrol DLN (commercially available from Bayer Corp., McMurray, Pa.), Bayhydrol LS-2033 (Bayer Corp.), Bayhydrol 123 (Bayer Corp.), Bayhydrol PU402A (Bayer Corp.), Bayhydrol 110 (Bayer Corp.), Witcobond W-320

(commercially available from Witco Performance Chemicals), Witcobond W-242 (Witco Performance Chemicals), Witcobond W-160 (Witco Performance Chemicals), Witcobond W-612 (Witco Performance Chemicals), Witcobond W-506 (Witco Performance Chemicals), NeoRez R-940 (commercially available from Zeneca Resins), NeoRez R-960 (Zeneca Resins), NeoRez R-962 (Zeneca Resins), NeoRez R-966 (Zeneca Resins), NeoRez R-967 (Zeneca Resins), NeoRez R-972 (Zeneca Resins), NeoRez R-9409 (Zeneca Resins), NeoRez R-9637 (Zeneca), NeoRez R-9649 (Zeneca Resins), and NeoRez R-9679 (Zeneca Resins).

The most preferred polyurethanes are aliphatic polyether polyurethanes. Examples of such aliphatic polyether polyurethanes include Sancure 2710® and/or Avalure UR 445®, Sancure 878®, NeoRez R-966, NeoRez R-967, and Witcobond W-320. The most preferred polyurethane for use in the present compositions is Sancure 2710® and/or Avalure UR 445®.

Examples of preferred polyacryls and polymethacryls include Gelva® 2497 (commercially available from Monsanto Co., St. Louis, Mo.), Duraplus® 2 (commercially available from Rohm & Haas Co., Philadelphia, Pa.), Joncryl® 95 (commercially available from S.C. Johnson Polymer, Sturtevant, Wis.), SCX-1537 (S. C. Johnson Polymer), SCX-1959 (S. C. Johnson Polymer), SCX-1965 (S. C. Johnson Polymer), Joncryl® 530 (S. C. Johnson Polymer), Joncryl® 537 (S. C. Johnson Polymer), Glascol LS20 (commercially available from Allied Colloids, Suffolk, Va.), Glascol C37 (Allied Colloids), Glascol LS26 (Allied Colloids), Glascol LS24 (Allied Colloids), Glascol LE45 (Allied Colloids), Carboset® CR760 (commercially available from BFGoodrich, Cleveland, Ohio), Carboset® CR761 (BFGoodrich), Carboset® CR763 (BFGoodrich), Carboset® 765 (BFGoodrich), Carboset® 19X2 (B1FGoodrich), Carboset® XL28 (BFGoodrich), Hycar 26084 (BFGoodrich), Hycar 26091 (BFGoodrich), Carbobond 26373 (BFGoodrich), Neocryl® A-601 (commercially available from Zeneca Resins, Wilmington, Mass.), Neocryl® A-612 (Zeneca Resins), Neocryl® A-6044 (Zeneca Resins), Neocryl® A-622 (Zeneca Resins), Neocryl® A-623 (Zeneca Resins), Neocryl® A-634 (Zeneca Resins), and Neocryl® A-640 (Zeneca Resins).

Examples of preferred urethane-acryl copolymers include Sancure® AU-4000 (commercially available from BFGoodrich), Sancure® AU-4010 (BFGoodrich), Witcobond A-100 (commercially available from Witco Performance Chemicals, Houston, Tex.), Witcobond W-610 (Witco Performance Chemicals), NeoPac R-9000 (commercially available from Zeneca Resins), NeoPac R-9030 (Zeneca Resins), and NeoPac R-9699 (Zeneca Resins).

Preferred volatile organic solvents have a boiling point of from about 50° C. to about 140° C., more preferably from about 56° C. to about 125° C., and most preferably from about 56° C. to about 98° C., at atmospheric pressure.

The compositions herein comprise one or more volatile organic solvents. The organic solvents herein are preferably water-miscible.

The more preferred organic solvents are selected from alcohols, esters, ketones, aromatic hydrocarbons, aliphatic hydrocarbons, and ethers having between one and about ten carbon atoms. Even more preferred organic solvents are selected from alcohols and esters having between one and about ten carbon atoms. Preferred alcohols are monohydric. The most preferred monohydric alcohols are selected from ethanol, iso-propanol, and n-propanol. The most preferred esters are selected from ethyl acetate and butyl acetate. Examples of other organic solvents include benzyl alcohol, amyl acetate, propyl acetate, acetone, heptane, iso-butyl acetate, iso-propyl acetate, toluene, methyl acetate, iso-butanol, n-amyl alcohol, n-butyl alcohol, hexane, and methyl ethyl ketone. Overall, the most preferred organic solvents are selected from iso-propanol, n-propanol, ethanol, ethyl acetate, butyl acetate, and acetone.

Wherein when the composition comprises greater than about 10% of the film-forming polymer, the composition comprises less than about 1% of iso-propanol, and preferably is substantially free of iso-propanol. By substantially free, it is meant that the composition comprises, by weight of the composition, less than about 0.5%, more preferably less than about 0.1% of iso-propanol.

Wherein a composition of the present invention comprises less than about 30%, by weight of the composition, of the organic solvent, the composition is substantially free of a fluorinated copolymer. By substantially free, it is meant that the composition comprises, by weight of the composition, less than about 0.5%, more preferably less than about 0.005% of a fluorinated copolymer.

The compositions of the present invention also include those prepared by a process of combining, in any order, the above specified components as well as any optional components as described herein.

The compositions of the present invention may further comprise information which informs a user of the composition, by words, pictures, and/or the like, that use of the composition will provide one or more long wear benefits, including, but not limited to, resistance to chipping, peeling, denting, and/or peeling.

The compositions of the present invention are preferably applied to mammalian nails to provide a basecoat, which is a layer of nail polish. The basecoat forms when a basecoat composition is applied to mammalian nails.

The layers herein are not peelable from the nails. That is, the compositions herein, when applied to a mammalian nail cannot be stripped off the nail by simply peeling the film off the nail in a substantially intact form.

Optional Components

The compositions of the present invention may comprise additional optional components to enhance their performance as a nail polish. For example, antifoams, buffers, chelating agents, coalescents, dispersing agents, dyes, epoxies, fillers, pigments, preservatives, resins, therapeutic and prophylactic agents, thickeners, wax additives, wetting agents, and the like can be included in the compositions herein. Such optional components may be dispersed, solubilized, or otherwise mixed in the carrier and/or the liquid diluent of the compositions. These components may be added to the compositions herein provided they do not substantially hinder the long wear properties, particularly the adhesion, of the compositions. Non-limiting examples of optional components are given below.

Coalescents

Coalescents may optionally be added to the present compositions to enhance film-formation. Such coalescing aids are known in the art and are typically glycol ethers or glycol ether esters such as $C_{1-10}$ straight or branched chain alkyl glycol alkyl ethers, $C_{1-10}$ straight or branched chain alkyl ether acetates, di-$C_{1-10}$ alkyl ether acetates, and $C_{1-10}$ alkyl glycol phenyl ethers. Preferred coalescing aids include, for example, ethylene glycol ethers (e.g., Dowanol EB®, commercially available from Dow Chemical Co.), diethylene glycol ethers, triethylene glycol ethers, propylene glycol ethers (e.g., Dowanol PnP®, Dow Chemical Co.), dipropylene glycol ethers (e.g., Dowanol DPnP®, Dow Chemical Co.), tripropylene glycol ethers, terpenes, camphor, methyl cellusolve, butyl cellusolve, hexyl cellusolve, methyl carbitol, butyl carbitol, and dibutyl phthalate.

Typically, coalescents are not needed in the compositions of the present invention. While the compositions of the present invention may comprise from 0% to about 10%, by weight of the composition, of a coalescent, the present compositions most preferably comprise 0%, by weight of the composition, of a coalescent.

Pigments or Dyes

Pigments and other suitable coloring agents may be incorporated into the present compositions. Suitable pigments are inorganic or organic pigments known as, for example, the FD&C and D&C colors, lakes, and iron oxides. Such pigments are disclosed in the C.T.F.A. *Cosmetic Ingredient Handbook,* First Edition, 1988. Organic pigments include, for example, D and C Red, Nos. 10, 11, 12, and 13, D and C Red No. 7, D and C Red Nos. 5 and 6, D and C Red Nos. 30 and 34, lacquers such as D and C Yellow No. 5 and D and C Red No. 2, and guanine. Inorganic pigments include, for example, titanium dioxide, bismuth oxychloride, brown iron oxide, and the red iron oxides.

Preferably, the present compositions comprise from 0% to about 5%, more preferably from 0% to about 2%, and most preferably from 0% to about 1%, by weight of the composition, of a pigment or dye.

Plasticizers

Without intending to be limited by theory, plasticizers cause a composition to become more easily deformed. One or more plasticizers may optionally be added to the present compositions. Suitable plasticizers include those disclosed in WO 97/00664, Chen et al, assigned to Eastman Chemical Co. Suitable plasticizers include phthalates, nonionic surfactant polymers, and polyesters. Preferred plasticizers include diethyl phthalate, dibutyl phthalate, dioctyl phthalate, diethyl tartrate, dibutyl tartrate, diethyl phosphate, dibutyl phosphate, polyester sebacates, such as Paraplex G-25® (commercially available from C. P. Hall, Bedford Park, Ill.) polyester adipates, such as Paraplex G-50® (C. P. Hall) and tetraethylene glycol di-2-ethylhexoate, available as Tegmer® (C. P. Hall). The most preferred plasticizers include dibutyl phthalate, Paraplex G-25®, Paraplex G-50®, and Tegmer®.

Typically, plasticizers are not needed in the compositions of the present invention. However, the compositions of the present invention may comprise from 0% to about 15%, more preferably from 0% to about 10%, and most preferably from about 0% to about 5%, by weight of the composition, of a plasticizer.

Preservatives

One or more preservatives may optionally be added to the present compositions to prevent, inhibit, or retard microbial growth in the composition. Preferably, the compositions comprise a preservative wherein the composition comprises less than about 40% of one or more organic solvents. Preferred preservatives include methyl paraben, ethyl paraben, propyl paraben, benzyl alcohol, benzoic acid, benzoates (preferably sodium benzoate), sorbates (preferably potassium sorbate), sodium dehydroacetate, 1-(3-chloroallyl)-3,5,7-triaza-1-azoniaadamantane chloride (which may be obtained commercially as Quatemium-15® from Dow Chemical Co., Midland, Mich.), a mixture of 95% 1,3-dimethylol-5,5-dimethyl hydantoin and 5% 3-iodo-2-propynyl butyl carbamate (which mixture is commercially available as Glydant Plus® from Lonza, Inc., Fair Lawn, N.J.), 1,3-dimethylol-5,5-dimethyl hydantoin (commercially available as Glydant® from Lonza, Inc.), diazolidinyl urea (commercially available as Germall II® from Sutton Laboratories, Chatham, N.J.), imidazolidinyl urea (commercially available as Germall 115® from Sutton Laboratories), phenoxyethanol, and Kathon® (commercially available from Rohm and Haas Co., Philadelphia, Pa.). The most preferred preservatives include methyl paraben, ethyl paraben, propyl paraben, benzyl alcohol, benzoic acid, benzoates (preferably sodium benzoate), sorbates (preferably potassium sorbate), and sodium dehydroacetate.

A composition preferably comprises from 0% to about 10%, more preferably from 0% to about 5%, and most preferably from 0% to about 1%, by weight of the composition, of a preservative.

Resins

Resins including, for example, epoxies and polyacrylics, may optionally be added. Examples of suitable resins include Polytex E75® (commercially available from Estron Chemical, Inc., Calvert City, Ky.) and Acryloid B66® (commercially available from Rohm and Haas, Philadelphia, Pa.).

A composition preferably comprises from 0% to about 15%, more preferably from about 0.5% to about 10%, by weight of the composition, of a resin.

Slip Aids

Slip aids may optionally be added to improve surface friction, water resistance, abrasion resistance, and mechanical properties. Slip aids which may be used include wax additives including, for example, animal, fossil, vegetable, mineral, or synthetic waxes. Preferred wax additives include beeswax, carob, candelilla, ozocerite, polyethylene waxes, paraffin waxes, polypropylene waxes, polytetrafluoroethylene (commercially available as Teflon® from DuPont, Wilmington, Del.), nylons, and polyamides. Specifically, preferred wax additives include, but are not limited to, Jonwax® 26 (commercially available from S. C. Johnson Polymer, Sturtevant, Wis.) Jonwax® 120 (S. C. Johnson Polymer), Chemcor 325N35, Chemcor 43N40, Glaswax® E-1 (commercially available from Allied Colloids, Suffolk, Va.), Glaswax® E-1235 (Allied Colloids), Drewax® E-3030 (commercially available from Ashland Chemical, Boontown, N.J.), Drewax® E-7030 (Ashland Chemical), Lanco® PP1362D (commercially available from Lubrizol, Wichliffe, Ohio), Lanco® A1601 (Lubrizol), and Lanco® TF1780 (Lubrizol).

Other slip aids include materials containing silicone such as copolymers of polyether and polysiloxane. Examples of such slip aids include, for example, Glide 450 and Abil B-8830 (both of which are commercially available from Goldschmidt Chemical, Hopewell, Va.).

The present compositions preferably comprise from 0% to about 10%, more preferably from about 0.1% to about 10%, even more preferably from about 0.5% to about 8%, and most preferably from about 0.5% to about 3% of a slip aid.

Therapeutic and Prophylactic Agents

Therapeutic and/or prophylactic agents such as, for example, vitamins, proteins, anti-fungal and anti-microbial agents, and sunscreens (including UV-A, UV-B, and broad spectrum solar filters) may optionally be added to the present compositions for the further care and protection of the nails.

Thickeners

Thickeners may optionally be added to the compositions and films herein to achieve desired rheology and application properties. Preferred thickeners include hydroxyethyl cellulose, hydroxypropyl cellulose, methyl cellulose, and other conventional cellulosic polymers, associative thickeners (e.g., hydrophobically modified cellulosic polymers, nonionic urethanes, and alkali swellable urethanes) including Aculyn® 44 (commercially available from Rohm & Haas, Philadelphia, Pa.), clays (e.g., laponite and hydrophilic montmorillonite (commercially available as Bentone® from Rheox, Hightstown, N.J.), and natural rubbers and gums (e.g., guar gum, quaternized guar gum sold under the name Jaguar® C-13-S by Rhone-Poulenc, Shelton, Conn.), hydroxypropyl guar gum, gum arabic, carob gum, carrageenan, and xanthan gum).

The present compositions preferably comprise from 0% to about 10%, more preferably from about 0.1% to about 10%, and even more preferably from about 0.1% to about 5% of a thickener, by weight of the composition.

Method of Making and Using

The compositions of the present invention are made using conventional formulation and mixing techniques. A layer of the present compositions may be prepared by standard application of a composition to mammalian nails using a standard brush-applicator as is commonly utilized in the art and removing sufficient liquid diluent (through evaporation of volatiles, most preferably at ambient pressures and temperatures) to form the substantially dry layer.

The present invention includes a method of coating mammalian nails with a nail polish film, wherein the film comprises one or more layers. The method comprises the steps of:

(i) applying a composition of the present invention (basecoat composition) contiguously to the nail, wherein the basecoat composition comprises a film-forming polymer and a carrier suitable for application to mammalian nails comprising a liquid diluent;
(ii) removing sufficient liquid diluent from the basecoat composition to form a substantially dry basecoat;
(iii) optionally applying a midcoat composition to the nail, wherein the midcoat composition comprises a film-forming polymer and a liquid diluent;
(iv) removing sufficient liquid diluent from the midcoat composition to form a substantially dry layer;
(v) optionally applying a topcoat composition to the nail, wherein the topcoat composition comprises a film-forming polymer and a liquid diluent; and
(vi) removing sufficient liquid diluent from the topcoat composition to form a substantially dry topcoat.

As used herein, a "midcoat composition" is a composition which is suitable for application to a mammalian nail to form a midcoat, which is a layer of nail polish. The midcoat composition is preferably applied contiguously to a preceding layer, either a basecoat or another midcoat, most preferably a basecoat. One or more succeeding layers is applied to the layer formed by the midcoat composition. Preferably, a topcoat is applied contiguously to the layer formed by the midcoat composition.

As used herein, a "topcoat composition" is a composition which is suitable for application to a mammalian nail to form a topcoat, which is a layer of nail polish. The topcoat composition is preferably applied contiguously to, or applied to, one or more preceding layers. The topcoat composition is more preferably applied contiguously to one or two, preferably one (basecoat), and most preferably two (basecoat and midcoat), preceding layers.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

In the examples herein below, all polymer component percentages are expressed in weight percent of solid polymer (based on the total composition).

EXAMPLES 1A–1J

The compositions of Examples 1A–1J are representative of the present invention:

| | Ex. 1A | Ex. 1B | Ex. 1C | Ex. 1D | Ex. 1E |
|---|---|---|---|---|---|
| Glascol LS20 | 6% | — | 9% | — | — |
| Glascol LS24 | — | — | — | — | 0.7% |
| NeoRez R-967 | 6% | — | — | 7.5% | — |
| Joncryl ® 95 | — | 6% | — | — | — |
| Sancure 2710 ® | — | 6% | 3% | — | 6% |
| SCX-1965 | — | — | — | 2.5% | — |
| Ethanol | 35% | 20% | 27% | 33% | 35% |
| Water | 53% | 68% | 61% | 57% | 58.3% |

| | Ex. 1F | Ex. 1G | Ex. 1H | Ex. 1I | Ex. 1J |
|---|---|---|---|---|---|
| Glascol LS28 | 0.7% | — | — | — | — |
| Glascol LS20 | — | — | — | — | 12% |
| Sancure ® AU-4000 | — | 7% | — | — | — |
| NeoPac R-9000 | — | — | — | 6% | — |
| Joncryl ® 95 | — | — | 10% | — | — |
| Sancure 2710 ® | 6% | — | — | — | — |
| Aculyn ® 44 | — | — | 0.5% | — | 0.5% |
| iso-Propanol | — | — | 19% | — | — |
| Ethanol | 30.5% | 15.2% | — | 33% | 29.3% |
| Water | 62.8% | 77.8% | 70.5% | 61% | 58.2% |

Example 2

A composition of Example 1 is applied contiguously to mammalian nails using a standard brush-applicator. A basecoat is allowed to form over a period of five minutes. A topcoat composition which is a conventional nail polish such as Max Factor® International (comprising butyl acetate, ethyl acetate, nitrocellulose, toluenesulfonamide formaldehyde resin, dibutyl phthalate, toluene, iso-propanol, camphor, benzophenone, stearalkonium hectorite, and polyester resin) is applied contiguously to the basecoat using a standard brush-applicator. The topcoat composition is allowed to form a topcoat over a five minute time period, resulting in a film having two layers.

Example 3

A composition of Example 1 is applied contiguously to mammalian nails using a standard brush-applicator. A basecoat is allowed to form over a period of five minutes. The topcoat composition described below is applied contiguously to the basecoat using a standard brush-applicator. The topcoat composition is allowed to form a topcoat over a five minute time period, resulting in a film having two layers.

| Component | Topcoat Composition | | |
|---|---|---|---|
| | Supplier Slurry Code* | Source | Percentage |
| Solid Nitrocellulose RS ¼ second (available as a slurry) | 50-C3-690 | Akzo Nobel, Somerset, NJ | 7.05% |
| Solid Nitrocellulose RS ½ second (available as a slurry) | 5528 | Scholle Corp., College Park, GA | 7.00% |
| Clay** (available as a slurry) | Bentone slurry | Kirker Enterprises Inc., Paterson, NJ | 1.04% |
| Red #7 Solid (available as a slurry) | Red #7 slurry 6R381 | Penn Color, Doylestown, PA | 0.60% |

-continued

Topcoat Composition

| Component | Supplier Slurry Code* | Source | Percentage |
|---|---|---|---|
| Butyl Acetate | | J. T. Baker, Phillipsburg, NJ | 27.77% |
| Ethyl Acetate | | J. T. Baker, Phillipsburg, NJ | 24.00% |
| iso-Propanol | | J. T. Baker, Phillipsburg, NJ | 6.55% |
| Uniplex 600 | | Unitex, Greensboro, NC | 11.12% |
| Toluene | | E. M. Science, Gibbstown, NJ | 6.44% |
| Camphor | | Universal Preservachem, Edison, NJ | 1.43% |
| Dibutyl Phthalate | | Eastman Kodak, Kingsport, TN | 7.00% |
| Total | | | 100.00% |

*The slurries contain, in addition to the component indicated, other components which are listed in the above formula (such as, for example, butyl acetate and iso-propanol). The percentage given for each component is the percentage of that component only (for example, Solid Nitrocellulose RS ¼ second is present in the control formula at a solids level of 7.05%, exclusive of other components). The levels of the other components in each slurry are combined and reflected in the formula given above. For example, the levels of butyl acetate in Nitrocellulose RS ¼ second slurry, Nitrocellulose RS ½ second slurry, clay, and Red #7 Solid are combined and reflected in the percentage given for the butyl acetate component.
**Clay is 50/50 (weight percent ratio) stearalkonium hectorite/stearalkonium bentonite solids.

The composition may be prepared as follows. Weigh all components together into a sealable jar to hold a 100 gram batch with minimal head-space. Add six stainless steel balls, each of which are 3/16 inches in diameter. Mix on a conventional paint shaker for thirty minutes. Transfer to conventional nail polish bottles.

The above topcoat composition may also be used as a midcoat composition with a basecoat composition having a composition of Example 1.

What is claimed is:

1. A nail polish composition comprising:
   (a) from about 0.1% to about 20%, by weight of the composition, of a water-insoluble film-forming polymer selected from the group consisting of polyacryls, polymethacryls, polyurethane-polyacryl mixtures, polyurethane-polymethacryl mixtures, urethane-acryl copolymers, and mixtures thereof; and
   (b) a carrier suitable for application to mammalian nails comprising a liquid diluent comprising:
      (i) from about 10% to about 90% by weight of the composition of a volatile organic solvent; and
      (ii) at least about 4% water;
   wherein when the composition comprises from about 10% to about 30%, by weight of the composition, of the organic solvent, the composition is substantially free of a fluorinated polymer and wherein when the composition comprises greater than about 10% of the polymer, the composition comprises less than about 1% of iso-propanol.

2. A composition according to claim 1 wherein the polymer is a urethane-acryl copolymer.

3. A composition according to claim 1 wherein the polymer is a polyacryl.

4. A composition according to claim 1 wherein the polymer is a polyurethane-polyacryl mixture.

5. A composition according to claim 1 comprising from about 1% to about 10% of the polymer.

6. A composition according to claim 5 wherein the organic solvent is selected from the group consisting of alcohols, esters, ketones, aliphatic hydrocarbons, aromatic hydrocarbons, and ethers having between one and about ten carbon atoms, and mixtures thereof.

7. A composition according to claim 6 wherein the organic solvent is selected from the group consisting of ethanol, iso-propanol, n-propanol, benzyl alcohol, ethyl acetate, n-butyl acetate, amyl acetate, propyl acetate, acetone, methyl ethyl ketone, heptane, iso-butyl acetate, iso-propyl acetate, toluene, methyl acetate, iso-butanol, n-amyl alcohol, n-butyl alcohol, hexane, and mixtures thereof.

8. A composition according to claim 7 wherein the organic solvent is selected from the group consisting of iso-propanol and n-propanol.

9. A composition according to claim 5 comprising from about 2% to about 6% of the polymer.

10. A composition according to claim 9 wherein the organic solvent is selected from the group consisting of alcohols, esters, ketones, aliphatic hydrocarbons, aromatic hydrocarbons, and ethers having between one and about ten carbon atoms, and mixtures thereof.

11. A composition according to claim 10 wherein the organic solvent is selected from the group consisting of ethanol, iso-propanol, n-propanol, benzyl alcohol, ethyl acetate, n-butyl acetate, amyl acetate, propyl acetate, acetone, methyl ethyl ketone, heptane, iso-butyl acetate, iso-propyl acetate, toluene, methyl acetate, iso-butanol, n-amyl alcohol, n-butyl alcohol, hexane, and mixtures thereof.

12. A composition according to claim 11 wherein the organic solvent is selected from the group consisting of iso-propanol and n-propanol.

13. A method of coating mammalian nails with a nail polish film comprising the steps of:
   (i) applying a composition according to claim 1 contiguously to the nail; and
   (ii) removing sufficient liquid diluent from the composition to form a substantially dry basecoat.

14. A method according to claim 13 further comprising the steps of:
   (iii) optionally applying a midcoat composition to the nail, wherein the midcoat composition comprises a film-forming polymer and a liquid diluent;
   (iv) removing sufficient liquid diluent from the midcoat composition to form a substantially dry layer;
   (v) applying a topcoat composition to the nail, wherein the topcoat composition comprises a film-forming polymer and a liquid diluent; and
   (vi) removing sufficient liquid diluent from the topcoat composition to form a substantially dry topcoat.

15. A composition according to claim 1 comprising from about I to about 15%, by weight of the composition, of the water-insoluble film forming polymer and at least about 25%, by weight of the composition, water.

16. A composition according to claim 15 wherein the film forming polymer is selected from the group consisting of polyacryls, polymethacryls, polyurethane-polyacryl mixtures, polyurethane-polymethacryl mixtures, and urethane-acryl copolymers.

17. A composition according to claim 16 comprising from about 15 to about 35% volatile organic solvent.

* * * * *